(12) United States Patent
Hossain et al.

(10) Patent No.: US 6,173,036 B1
(45) Date of Patent: Jan. 9, 2001

(54) DEPTH PROFILE METROLOGY USING GRAZING INCIDENCE X-RAY FLUORESCENCE

(75) Inventors: Tim Z. Hossain, Austin; Don A. Tiffin, The Colony, both of TX (US); Cornelia A. Weiss, Hartmannsdorf (DE)

(73) Assignee: Advanced Micro Devices, Inc., Sunnyvale, CA (US)

( * ) Notice: Under 35 U.S.C. 154(b), the term of this patent shall be extended for 0 days.

(21) Appl. No.: 09/127,281

(22) Filed: Jul. 31, 1998

Related U.S. Application Data

(60) Provisional application No. 60/054,605, filed on Aug. 1, 1997.

(51) Int. Cl.[7] ................................................. G01N 23/223

(52) U.S. Cl. ................................................. 378/45; 378/50

(58) Field of Search ........................................... 378/45–50

(56) References Cited

U.S. PATENT DOCUMENTS

| | | | |
|---|---|---|---|
| 4,169,228 | * 9/1979 | Briska et al. | 378/50 |
| 5,164,093 | 11/1992 | Chilton et al. | 210/688 |
| 5,373,544 | 12/1994 | Goebel | 378/71 |
| 5,497,407 | 3/1996 | Komatsu et al. | 378/45 |

OTHER PUBLICATIONS

*Minutes of ISO/TC201/WG2 on Total Reflection X–Ray Fluorescence Spectroscopy*, ISO/TC 201/WG2 N 27, Jan. 29, 1996.

*Third Working Draft, Surface Chemical Analysis—Determination Of Contamination Elements Contents On Silicone Wafer–Total Reflections X–Ray Fluorescence Spectroscopy (TXRF)*, ISO/TC 201/WG2 N 26, Nov. 27, 1995.

R. S. Hockett, Proceedings from the Denver X–Ray Conference, *An Update on Standards Activity for TXRF and the Challenges Ahead*, Aug. 1995, pp. 1–4.

R.S. Hockett, TXRF Detection of Subsurface Metals in Silicon Substrates, in the Proceedings of the Symposium on *Diagnostic Techniques for Semiconductor Materials and Devices*, vol. 92–9, pp. 132–139.

Kenji Yakushiji et al., Main Peak Profiles of Total Reflection X–Ray Fluorescence Analysis of Si(001) Wafers Excited by Monochromatic X–Ray Beam W–Lβ (II), Jpn. J. Appl. Phys. vol. 32 (1993) pp. 1191–1196.

(List continued on next page.)

Primary Examiner—Craig E. Church
(74) Attorney, Agent, or Firm—Skjerven Morrill MacPherson LLP; Ken J. Koestner

(57) ABSTRACT

For small angles that are near critical angle, a primary incident X-ray beam has excellent depth resolution. A series of X-ray fluorescence measurements are performed at varying small angles and analyzed for depth profiling of elements within a substrate. One highly useful application of the X-ray fluorescence measurements is depth profiling of a dopant used in semiconductor manufacturing such as arsenic, phosphorus, and boron. In one example, angles are be varied from 0.01° to 0.20° and measurements made to profile arsenic distribution within a semiconductor wafer. In one embodiment, measurements are acquired using a total reflection X-ray fluorescence (TXRF) type system for both known and unknown profile distribution samples. The fluorescence measurements are denominated in counts/second terms and formed as ratios comparing the known and unknown sample results. The count ratios are compared to ratios of known to unknown samples that are acquired using a control analytical measurement technique. In one example the control technique is secondary ion mass spectroscopy (SIMS) so that the count ratios from the TXRF-type measurements are compared to ratios of integrals of SIMS profiles. In another example, the TXRF-type measurement ratios are compared to simulation profiles of known samples. Integrals of the SIMS profile that vary as a function of depth into the substrate correspond to the grazing incidence angles of the TXRF-like measurement and respective count rates.

13 Claims, 11 Drawing Sheets

OTHER PUBLICATIONS

D.K.G. de Boer, Glancing–Incidence X–Ray Fluorescence of Layered Materials, © 1991 The American Physical Society, vol. 44, No. 2, pp. 498–511.

H. Schwenke et al., Treatment of Roughness and Concentration Gradients in Total Reflection X–Ray Fluorescence Analysis of Surfaces, Applied Physics A 54, © Springer–Verlag 1992, pp. 460–465.

J. Knoth et al., Examination of Layered Structures by Total–Reflection X–Ray Fluorescence Analysis, Spectrochimica Aeta, vol. 48B, No. 2, pp. 285–292—© 1993.

Peter Eichinger, Total Reflection X–Ray Fluorescence Analysis, X–Ray Emission Techniques, Chapter 6—TXRF—pp. 349–356.

Paul K. Chu, Dynamic Secondary Ion Mass Spectrometry, Chapter 10—Dynamic SIMS—Mass and Optical Spectroscopies, pp. 532–548.

G. Wiener et al., Concentration–Depth Profiling Using Total–Reflection X–Ray Fluorescence Spectrometry In Combination With Ion–Beam Microsectioning Techniques, Rev. Sci. Instrum., vol. 68, No. 1, Jan. 1995, pp. 20–23.

* cited by examiner

DEPTH PROFILE METROLOGY USING GRAZING INCIDENCE X-RAY FLUORESCENCE

This application claims benefit to Provisional Application 60/054,605 filed Aug. 1, 1997.

BACKGROUND OF THE INVENTION

1. Field of the Invention

The present invention relates to measurement techniques used in semiconductor processing and fabrication. More precisely, the present invention relates to nondestructive measurement techniques for determining implant dose in semiconductor devices.

2. Description of the Related Art

In semiconductor processing and fabrication arts, considerable investment has been made in developing high resolution measurement devices and techniques for evaluating sample parameters. Many various types of measurements are performed in the semiconductor industry where very thin films, such as oxides, metals or dielectrics, are deposited on semiconductor substrates such as silicon. Non-destructive techniques are particularly useful for evaluating thickness, impurities and index of refraction characteristics of the films to insure high yields during fabrication.

One type of information that is particularly useful in semiconductor fabrication is information relating to the dose and profile of ion implantation of dopants such as arsenic (As), phosphorus (P), and boron (B). One conventional technique for monitoring implant dose is ellipsometry which measures damage that results from implantation. In another conventional technique, implant doses are monitored using a Faraday cup or cage in the implanter. Ellipsometry and Faraday cup techniques are nondestructive tests. In contrast, implant profiles are usually measured using a secondary ion mass spectometry (SIMS) laboratory set-up outside the fab.

Conventional ellipsometric techniques are non-contact, optical measurement techniques. A probe beam having a known polarization state is directed to interact with a sample, resulting in a change in the polarization state that is monitored by measuring a selected parameter of the reflected probe beam. For example, as the thickness of a film varies, the intensity of the reflected probe beam also varies due to the variation in interference effects created at the interface between the thin film and the substrate. Also the thickness of a thin film changes the polarization state which occurs when the probe beam is reflected off the sample surface. By monitoring either the change in intensity of the reflected probe beam or the change in polarization state (ellipsometry), information about the thin film is derived. An analyzer determines the polarization state of the beam following the beam interaction with the sample. The change in polarization state of the beam caused by the interaction with the sample varies as a function of the sample parameters. Measurement of the change supplies data used in analysis of the sample. In a typical measurement scenario, the azimuthal angle of the polarizing or analyzing elements are varied to obtain multiple measurements. Usage of multiple measurements increases accuracy. One approach for improving accuracy is to perform measurements at several different wavelengths using a spectrophotometer that performs multiple-wavelength interferometric-type measurements. Another approach for improving accuracy is to measure at a number of different incidence angles of the probe beam.

Faraday cages trap and measure ion beam current during implanting while blocking electrons that might accompany the ion beam. Faraday cages do not measure neutral atoms in the ion beam. Since neutralized atoms have essentially the same energy as the ions and are individually equivalent in terms of implantation dose, if significant neutralization of the beam takes place, the Faraday cage reading expresses a false measure of the implantation current. The Faraday cage determines a sensed beam intensity of an ion beam at the target chamber. An implant controller determines beam current from the sensed beam intensity by accounting for both charge stripping and charge neutralization of ions within the ion beam caused by interactions between the ions that make up the beam and residual gas molecules encountered by the beam along the beam path to the target.

Secondary ion mass spectroscopy (SIMS) is a prevalent analytical method in the microelectronics industry today for characterizing materials present in semiconductor processes. In SIMS, a sample to be studied is bombarded with a primary beam of energetic ions. The ions sputter away ionized particles, for example secondary ions, from the surface of the sample. The secondary ions are directed into a mass spectrometer which identifies the ions as a function of a mass to charge ratio. Continued sputtering dislodges particles and secondary ions located below the surface of the sample. Thus, SIMS permits analysis of elements embedded within the sample as a function of sample depth. For example, SIMS data may express that $10^{19}$ atoms of boron per $cm^2$ reside at the surface of a silicon sample while $10^{19}$ atoms of boron per $cm^2$ reside one micron below the surface. SIMS is presently used to measure the amount of material embedded within a thin film. However, SIMS does not meet the requirements of being an inexpensive, non-destructive technique requiring little maintenance, having the ability to serve as a portable monitoring station.

Although SIMS depth resolution, lateral resolution, and sensitivity continue to improve as technology advances, several drawbacks are inherent with SIMS measurements. The biggest drawback is SIMS character as a destructive technique. SIMS sputters away layer after layer of material from the surface of the sample. Thus SIMS is not feasible for usage as a bench-top process control station for monitoring the amount of material embedded within a substrate. Furthermore, SIMS is a very bulky, complex, expensive method that employs complicated, maintenance-intensive machinery. For instance, SIMS instruments typically occupy an entire room in a midsized laboratory and include several vacuum pumps, valves, powerful magnets, energy filters, ion sources, and complex data analysis tools.

What is needed is an analytical method that measures the implant dose nondestructively.

SUMMARY OF THE INVENTION

It has been discovered that, for small angles that are near critical angle, a primary incident X-ray beam has excellent depth resolution. A series of X-ray fluorescence measurements are performed at varying small angles and analyzed for depth profiling of elements within a substrate. One highly useful application of the X-ray fluorescence measurements is depth profiling of a dopant used in semiconductor manufacturing such as arsenic, phosphorus, and boron. In one example, angles are to be varied from 0.01° to 0.20° and measurements made to profile arsenic distribution within a semiconductor wafer.

In one embodiment, measurements are acquired using a total reflection X-ray fluorescence (TXRF) type system for both known and unknown profile distribution samples. The fluorescence measurements are denominated in counts/ second terms and formed as ratios comparing the known and unknown sample results. The count ratios are compared to ratios of known to unknown samples that are acquired using a control analytical measurement technique. In one example the control technique is secondary ion mass spectroscopy (SIMS) so that the count ratios from the TXRF-type measurements are compared to ratios of integrals of SIMS profiles. In another example, the TXRF-type measurement ratios are compared to simulation profiles of known samples. Integrals of the SIMS profile that vary as a function of depth into the substrate correspond to the grazing incidence angles of the TXRF-like measurement and respective count rates.

Thus, total reflection X-ray fluorescence (TXRF) is newly employed and highly useful as a nondestructive technique for in-line shallow implant dose and profile monitoring. Total reflection X-ray fluorescence (TXRF) is a useful tool for rapid, nondestructive monitoring of implant doses including, but not limited to arsenic (As), boron (B), boron fluoride ($BF_2$), and phosphorus (P), in semiconductor manufacturing. A fluorescence yield (FY) measurement by TXRF, a nondestructive technique, is calibrated using a corresponding destructive measurement technique such as secondary ion mass spectroscopy (SIMS). The comparison between TXRF and SIMS demonstrates a substantial correlation and permits determination of a calibration coefficient for nondestructive testing of in-line shallow implant dose and profile determination.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

The use of the same reference symbols in different drawings indicates similar or identical items.

DESCRIPTION OF THE PREFERRED EMBODIMENT(S)

Figure 1:
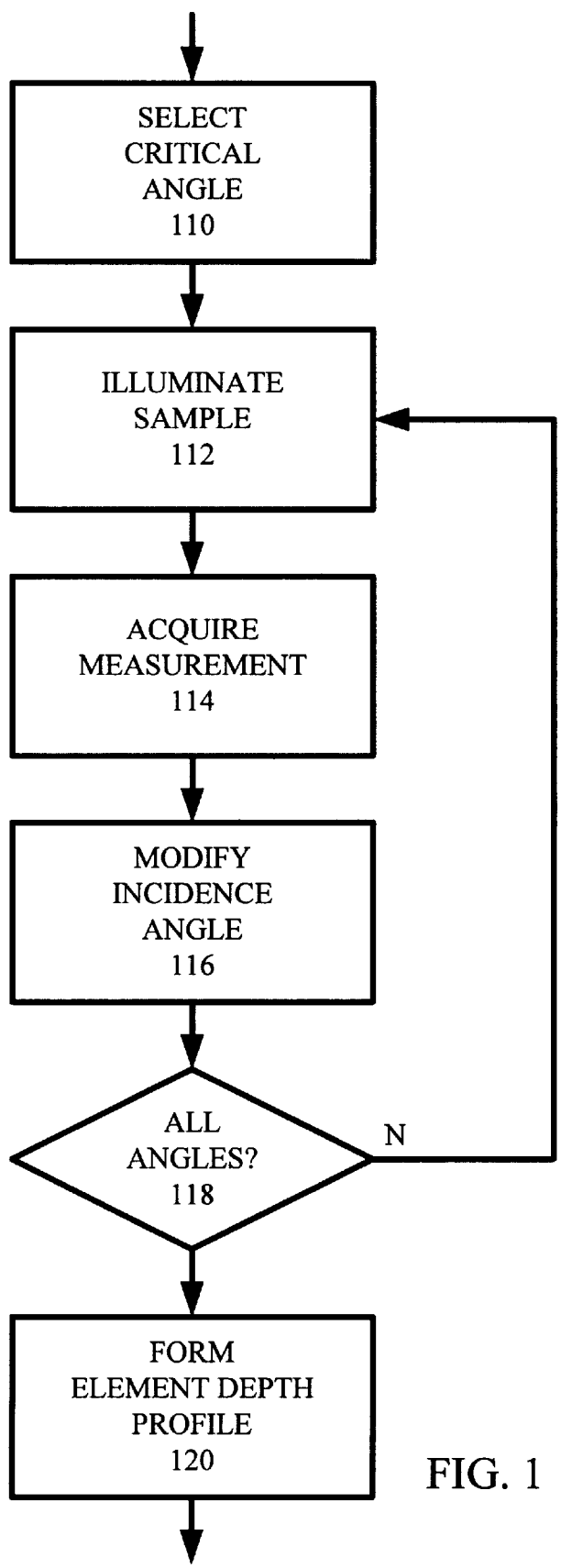
FIG. 1 is a schematic flow chart that illustrates a method for determining depth profiles and implant dose for a selected element in accordance with a first aspect of the present invention.

Referring to FIG. 1 a schematic flow chart that illustrate a method for determining depth profiles and implant dose for a selected element. A primary incident X-ray beam has excellent depth resolution at small angles near a critical angle of total reflection $\phi_{crit}$ that is selected according to the material to be analyzed in a select critical angle operation 110. In one application, X-ray fluorescence measurements are performed to profile the depth of a dopant used in semiconductor manufacturing such as arsenic, phosphorus, and boron. An X-ray beam is employed to illuminate a substrate sample at a selected incident angle that is a small angle near the critical angle $\phi_{crit}$ in an illuminate sample operation 112. An X-ray fluorescence measurement is acquired at the selected incident angle and stored in an acquire measurement operation 114. Following acquisition of a sample, the angle of incidence is modified in preparation for a subsequent sample in a modify incidence angle operation 116. The illuminate sample operation 112, the acquire measurement operation 114, and the modify incidence angle operation 116 are repeated several times for a selected plurality of small angles near the critical angle $\phi_{crit}$ in a sample looping operation 118. When measurements for all angles are acquired, a depth profile distribution is formed as a function of the acquired measurements in a form element depth profile operation 120.

The series of X-ray fluorescence measurements are performed at multiple varying small angles and analyzed for depth profiling of a selected element within a substrate. In one example, angles are be varied from 0.01° to 0.20° and measurements made to profile arsenic (As) distribution within a semiconductor wafer. In other examples, distributions for common semiconductor dopants are determined including distributions for boron (B), phosphorus (P), and boron fluoride ($BF_2$).

Figure 2:
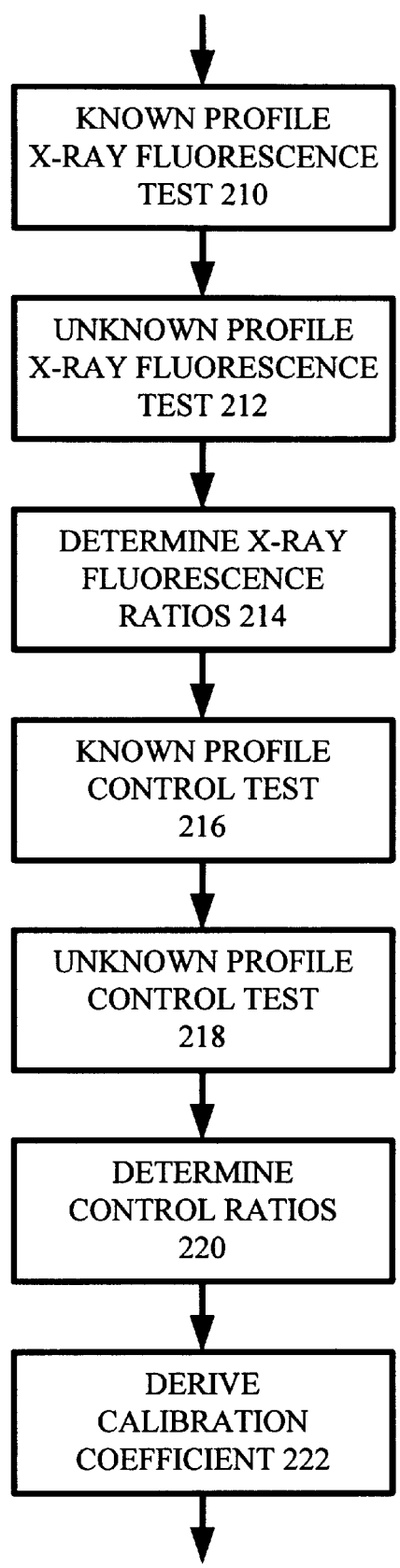
FIG. 2 is a schematic flow chart that shows a method for determining depth profiles and implant dose for a selected element in accordance with a second aspect of the present invention.

Referring to FIG. 2, a schematic flow chart shows another aspect of a method for determining depth profiles and implant dose for a selected element. The illustrative technique determines a set of parameters indicative of a correspondence between fluorescence and dopant concentration. Conventional techniques for accurately determining dopant concentration are destructive tests that are unsuitable for testing of samples in a fabrication facility. In contrast, fluorescence measurements are nondestructive and advantageously may be performed on production samples. An illustrative method for measuring a depth profile of an element in a substrate begins by acquiring a plurality of first X-ray fluorescence measurements from a test substrate with a known implant profile distribution for a selected element in a known profile X-ray fluorescence test operation 210.

Similarly, an unknown profile X-ray fluorescence test operation 212 is performed to acquire a plurality of second X-ray fluorescence measurements from a test substrate having an unknown implant profile distribution for the selected element. In a determine X-ray fluorescence ratios operation 214, a plurality of X-ray fluorescence ratios are set by comparing the first X-ray fluorescence measurements from testing of known profile substrates and the second X-ray fluorescence measurements from testing of unknown profile substrates.

Similarly control measurements are performed on substrates with the known and unknown depth profiles. In a known profile control test operation 216, a plurality of first control measurements are performed using a test substrate having the known implant profile distribution for the selected element. In an unknown profile control test operation 218, a plurality of second control measurements are performed using a test substrate having the unknown implant profile distribution for the selected element. A determine control ratios operation 220 sets a plurality of control ratios by comparing the first control measurements from testing of known profile substrates and the second control measurements from testing of unknown profile substrates. The fluorescence measurements and the control measurements are used to correlate angular dependence of the fluorescence yield with concentration of surface impurities. Calibration coefficients are derived by comparing the plurality of X-ray fluorescence ratios and the plurality of control ratios in a derive calibration coefficient operation 222.

In one system, the X-ray fluorescence measurements are acquired using a total reflection X-ray fluorescence (TXRF) type system for both known and unknown profile distribution samples in the known profile X-ray fluorescence test operation 210 and the unknown profile X-ray fluorescence test operation 212, respectively. The fluorescence measurements are denominated in counts/second terms and formed as ratios comparing the known and unknown sample results. The count ratios are compared to ratios of known to unknown samples that are acquired using a control analytical measurement technique. In one example, the control technique is secondary ion mass spectroscopy (SIMS) so that the count ratios from the TXRF-type measurements are compared to ratios of integrals of SIMS profiles in the derive calibration coefficient operation 222. Integrals of the SIMS profile that vary as a function of depth into the substrate correspond to the grazing incidence angles of the TXRF-like measurement and respective count rates. SIMS measurements supplies a template that substantially forms a one-to-one correlation between fluorescence yield and impurity concentration. SIMS measurements are used to empirically determine relationship of fluorescence yield to impurity concentration that is substantially exact.

In another example, the TXRF-type measurement ratios are compared to simulation profiles of known samples.

Figure 3:
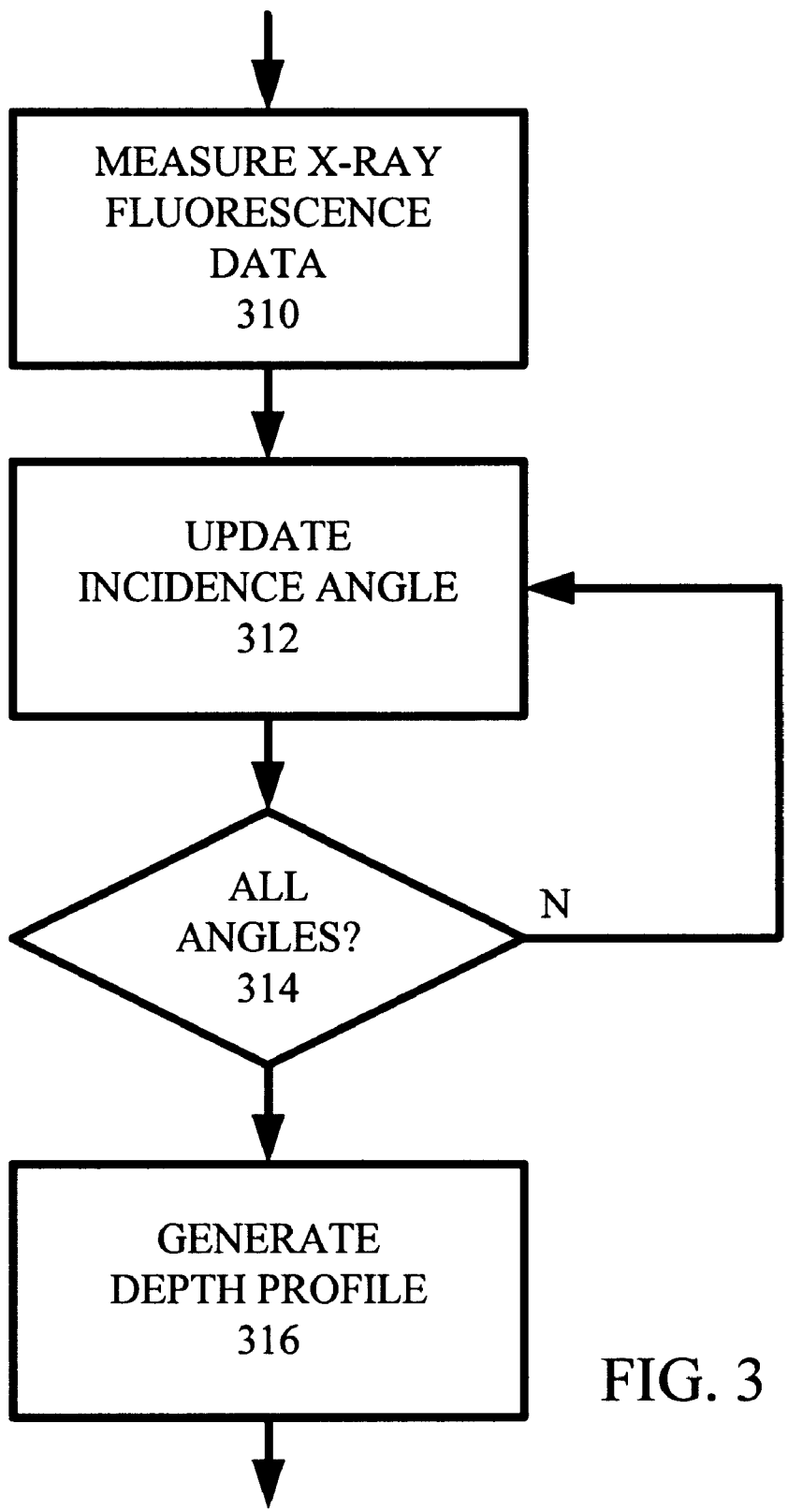
FIG. 3 is a schematic flow chart depicting a nondestructive method for determining depth profiles and implant dose for a selected element using a predetermined calibration coefficient.

Referring to FIG. 3, a schematic flow chart depicts a nondestructive method for determining depth profiles and implant dose for a selected element using a calibration coefficient that is determined using another technique, such as a destructive technique. In the illustrative system, a first set of parameters, here the relationship between fluorescence and dopant concentration, is determined destructively using secondary ion mass spectroscopy (SIMS). Once the relationship is obtained, the nondestructive technique is used to examine similar samples by fluorescence alone, for example using angular-resolved TXRF to probe for the measured element at different depths by changing the angle of incidence of the measurement. In a measure X-ray fluorescence data step 310, a substrate sample is illuminated with an X-ray beam at a selected angle of incidence and a fluorescence yield measurement is acquired and stored. The angle of incidence of the X-ray beam is varied within selected small angles near the critical angle of total reflection $\phi_{crit}$ in an update incidence angle operation 312. Differing the angle of incidence results in implant dose measurements at different depths in the substrate. Fluorescence data acquired at multiple depths are acquired in a looping operation 314 that returns to the measure X-ray fluorescence data step 310. In a generate depth profile operation 316, a depth profile distribution of the measured element is formed as a function of the acquired X-ray fluorescence data and the calibration coefficient.

Total reflection X-ray fluorescence (TXRF) is discovered to be a highly useful nondestructive technique for in-line shallow implant dose and profile monitoring in semiconductor processing. Total reflection X-ray fluorescence (TXRF) is a useful tool for rapid, nondestructive monitoring of implant doses including, but not limited to arsenic (As), boron (B), boron fluoride ($BF_2$), and phosphorus (P), in semiconductor manufacturing. A fluorescence yield (FY) measurement by nondestructive TXRF is calibrated using a corresponding destructive measurement technique such as secondary ion mass spectroscopy (SIMS). The comparison between TXRF and SIMS is substantially correlated and permits determination of a calibration coefficient for nondestructive testing of in-line shallow implant dose and profile determination.

X-ray Fluorescence (XRF) is a measurement technique in which a beam of primary X-rays is directed at the surface of a sample and the energy levels or corresponding wavelengths of resultant secondary X-rays emitted by atoms of elements on and under the surface of the sample are measured. Elemental compositions of materials on and under the surface of the wafer are determined from the measured energy levels or wavelengths of emitted secondary X-rays.

Two categories of XRF are wavelength-dispersive XRF (WDXRF) and energy-dispersive XRF (EDXRF). In WDXRF techniques, a sample is irradiated with polychromatic primary X-rays and resultant secondary X-rays are dispersed by diffraction into discrete wavelengths. Intensities of the secondary X-ray photons are measured against wavelength. Elements as small as boron may be measured by performing WDXRF in a vacuum. EDXRF techniques involve irradiating a sample with polychromatic primary X-rays and measuring fluorescent secondary X-ray intensity against detected secondary X-ray photon energy level. Elements as small as sodium may be measured by performing WDXRF with commercially-available equipment.

A disadvantage of XRF is the presence of background radiation which limits the sensitivity. Primary X-ray photons typically lose energy when scattered by atoms of the target material. The X-ray detector senses some of the scattered primary X-ray photons, generating an unwanted background intensity level. Sensitivity of an XRF instrument is improved by reducing the amount of scattered primary X-rays reaching the detector, usually by employing more powerful, collimated, polarized sources of primary X-rays. Improved sensitivity XRF devices detect trace concentrations of elements as low as approximately $10^{11}$ atoms/cm$^2$.

Another disadvantage of XRF machines is the degree of penetration into a sample. XRF machines employing high-powered X-ray sources excite atoms well below the surface of the sample so that secondary X-ray photons emitted by the sample may originate a few microns from the surface of the sample. A more desirable technique confines measurements to near the surface and does not penetrate to lower levels of the substrate.

Total reflection X-ray fluorescence (TXRF) advantageously has a limited depth of penetration into the substrate. In comparison to conventional X-ray fluorescence (XRF) tools, which use an angle of incidence of about 45°, the angle of incidence for TXRF is below the critical angle of total reflection $\phi_{crit}$. Depending on the analyzed material, $\phi_{crit}$ is in a range from about 0.01° to approximately 0.15°. For angles in this range, only information from the shallow region of the analyzed material is obtained. In comparison to conventional XRF, the background in TXRF studies is decreased so that the detection limit is lowered.

Figure 4:
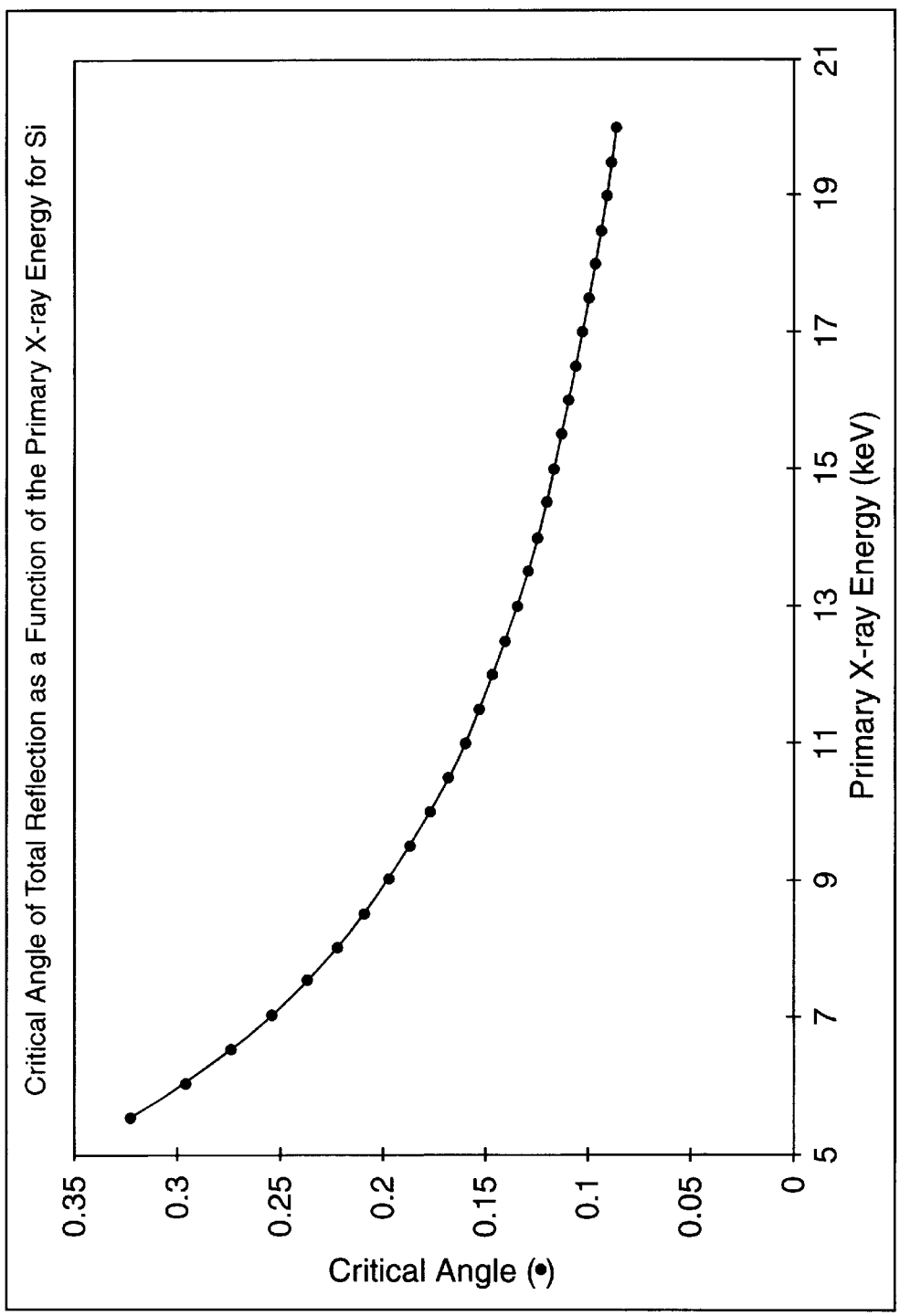
FIG. 4 is a graph showing a calculated value of critical angle of total reflection $\phi_{crit}$ as a function of primary X-ray energy for silicon.

The physics of total reflection is described by using three parameters including critical angle of total reflection $\phi_{crit}$, depth penetration $z_n$ of the X-rays, and reflectivity R. The critical angle of total reflection $\phi_{crit}$ is a function of incoming X-ray beam energy and varies according to the material that is analyzed. Equation (1) describes the critical angle of total reflection $\phi_{crit}$ as follows:

$$\phi_{crit} \approx \frac{1.65}{E} p \sqrt{\frac{Z}{A}}, \quad (1)$$

where E is the energy of the primary X-ray beam and $\rho$ is the density, Z is the atomic number, and A is the atomic weight of the sample. FIG. 4 is a graph that shows a calculated value of critical angle of total reflection $\phi_{crit}$ as a function of primary X-ray energy for silicon. The graph shows that the critical angle of total reflection $\phi_{crit}$ is approximately 0.15° at a primary X-ray energy of 12 keV.

The penetration depth $z_n$ of the TXRF measurement is determined by the penetration depth of the primary X-ray beam. The penetration depth $z_n$ at an angle of incidence $\phi$ is given by equation (2), as follows:

$$Z_n = \frac{\lambda}{4\pi\eta}, \quad (2)$$

where $\lambda$ is the wavelength of the primary X-rays and n is the refractive index which is determined according to equation (3), as follows:

$$\eta^2 = \frac{1}{2}\left[\sqrt{|(\phi^2 - 2\delta)^2 + (2\beta)^2|} - (\phi^2 - 2\delta)\right], \quad (3)$$

Figure 5:
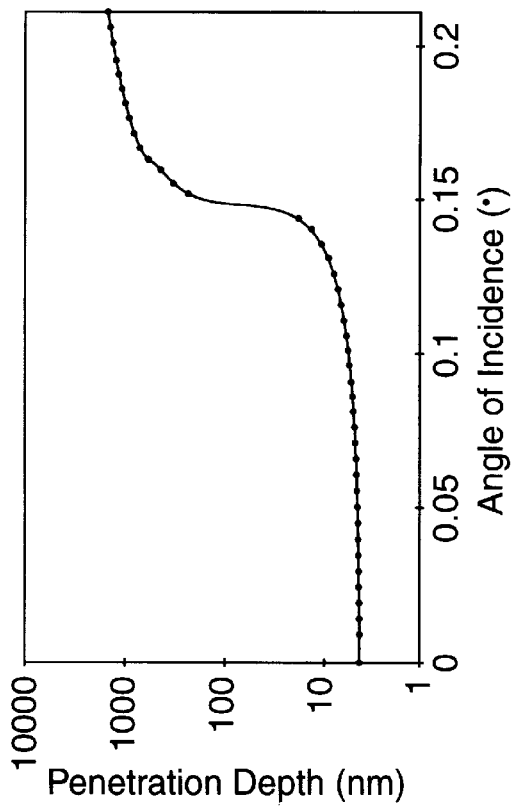
FIG. 5 is a graph showing penetration depth of the primary X-ray beam as a function of the angle of incidence $\phi$ for silicon at a primary X-ray energy of 12 keV.

Referring to FIG. 5, a graph shows penetration depth of the primary X-ray beam as a function of the angle of incidence $\phi$ for silicon at a primary X-ray energy of 12 keV. The penetration depth as beam intensity is decreased to 1/e is approximately 4 nm for $\phi$<0.1°, but it jumps at the critical angle ($\phi_{crit}\approx$0.15°) and passes over into the XRF penetration depth.

Figure 6:
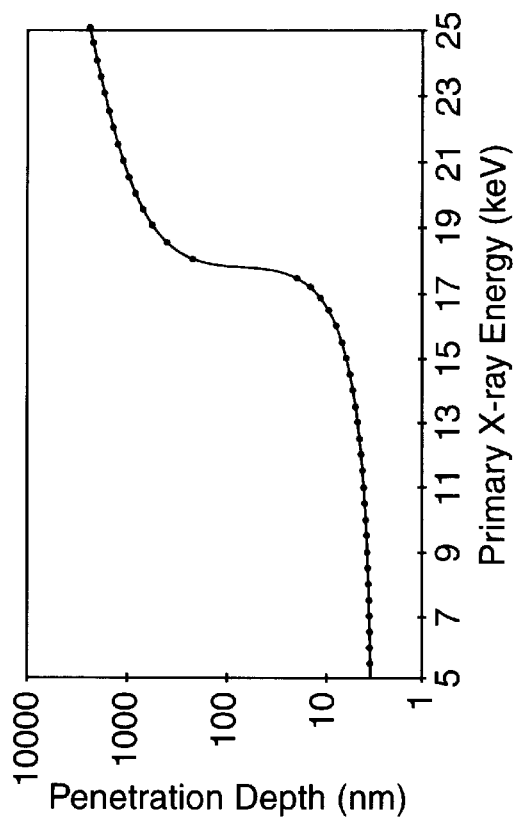
FIG. 6 is a graph showing penetration depth of the primary X-ray beam as a function of primary X-ray energy for silicon at an angle of incidence $\phi$ of 0.1°.

Referring to FIG. 6, a graph shows penetration depth of the primary X-ray beam as a function of primary X-ray energy for silicon at an angle of incidence $\phi$ of 0.1°. For an energy of 17.5 keV, the critical angle of total reflection $\phi_{crit}$ is approximately 0.1°, an angle at which the depth penetration of the primary beam is extremely increased. Thus, the depth penetration greatly increases at approximately the 17.5 keV energy level.

Equation (3) includes components $\beta$ and $\delta$, which are defined by the complex refractive index n in equation (4), as follows:

$$n=1-\beta-i\delta, \quad (4)$$

Referring again to FIG. 5, penetration depth $z_n$ of the primary X-rays into silicon (Si) at a primary X-ray energy of 12 keV is approximately 6 nm as long as the angle of incidence $\phi_i$ less than 0.1°. Beam divergence is not considered in the analysis.

Reflectivity R is derived from the Fresnel Equations shown in equation (5), as follows:

$$R = \frac{(\phi - \varepsilon)^2 + \eta^2}{(\phi + \varepsilon)^2 + \eta^2}, \quad (5)$$

where $$\varepsilon^2 = \frac{1}{2}\left[\sqrt{|(\phi - 2\delta)^2 + (2\beta)^2|} - (\phi - 2\delta)\right], \quad (6)$$

Figure 7:
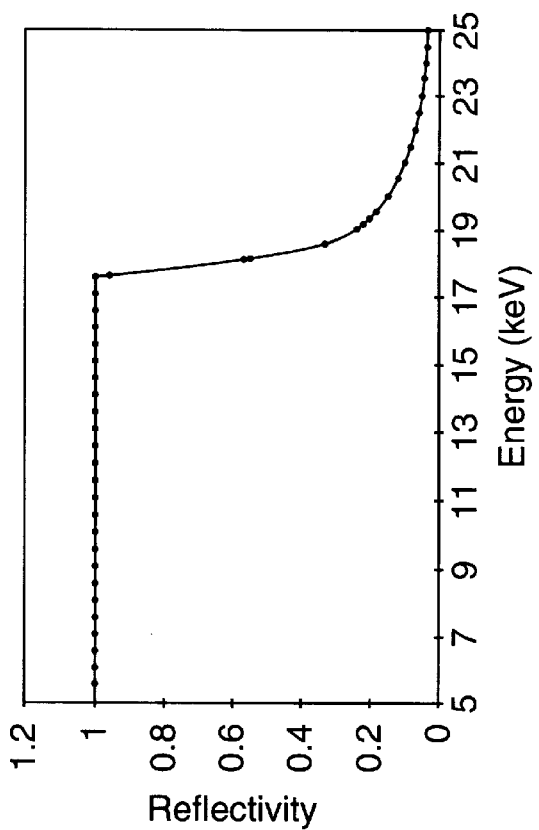
FIG. 7 is a graph depicting the energy dependence of the reflectivity R for silicon at an incidence angle $\phi_i$ of 0.1°.

Referring to FIG. 7, a graph depicts the energy dependence of the reflectivity R for silicon at an incidence angle $\phi_i$ of 0.1°. Reflectivity is depicted as a function of the primary X-ray energy for Silicon (Si) at an angle of incidence $\phi_i$ of 0.1°. According to FIGS. 5 and 6, the critical angle of total reflection $\phi_{crit}$ is 0.1° for 17.5 keV. At the energy of 17.5 keV, the reflectivity R greatly decreases and a dominant part of the X-ray beam is absorbed by the substrate.

Figure 8:
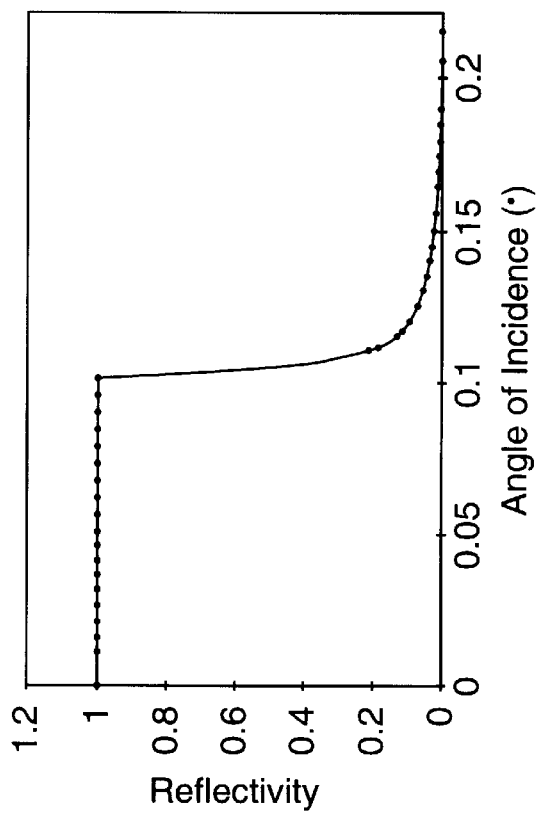
FIG. 8 is a graph showing reflectivity R as a function of the angle of incidence $\phi_i$ for silicon at a primary beam energy of 17.5 keV.

Referring to FIG. 8, a graph depicts reflectivity R as a function of the angle of incidence $\phi_i$ for silicon at a primary beam energy of 17.5 keV. At the critical angle of total reflection $\phi_{crit}$ of 0.1°, the reflectivity R decreases and a dominant part of the X-ray beam is absorbed rather than reflected.

The reflectivity of X-rays is nearly zero above the critical angle of total reflection $\phi_{crit}$, and nearly one below $\phi_{crit}$. The fluorescence yield (FY) intensity when the angle of incidence $\phi_i$ is less than the critical angle of total reflection $\phi_{crit}$ is approximately twice the FY intensity when the angle of incidence exceeds the critical angle of total reflection $\phi_{crit}$. The doubling of fluorescence yield occurs because particles are excited equally by the incoming beam and the reflected beam, as is shown in FIGS. 7 and 8. As the FY intensity of the trace element i is independent of the angle of incidence in the region of total-reflection. A measurement performed at a single angle of incidence is sufficient to describe all angles of incidence $\phi_i$ less than the critical angle of total reflection $\phi_{crit}$.

TXRF has been previously used in semiconductor industry for metallic trace contamination analysis of wafer surfaces that result from contamination from different process steps of device manufacturing. For the case of metallic contamination detection, the measured FY intensity of the trace element is described by equation (7), as follows:

$$I_{FY(a)}=Kc_i[1+R], \quad (7)$$

where K is a normalization constant and $c_i$ is the area-related concentration of the element i described in atoms/cm$^2$. Detection limits of TXRF about 2×10$^9$ atoms/cm$^2$ for Fe, Ni and Cu and in the low 10 atoms/cm$^2$ for many other metals. The nondestructive nature of the method, minimal or no sample preparation, and rapid turnaround time makes TXRF an attractive surface analytical tool for high volume manufacturing. However, until the present system and technique was discovered, TXRF was practically limited by the detection of elements with low atomic numbers (Z<4).

In the illustrative measurement technique and in contrast to real surface applications, TXRF data from at least two different angles of incidence $\phi_i$ less than $\phi_{crit}$ are used for implant dose characterization. FIG. 5 illustrates that angle of incidence angles $\phi_i$ are chosen in a range between $0.8\phi_{crit}$ and $\phi_{crit}$. The suitable range of angles is obtained when the angle divergence of the primary X-ray beam is small. Good X-ray beam collimation is attained in fabrication TXRF systems by special X-ray optical elements or by using synchrotron radiation beam lines.

In an illustrative example of the TXRF technique, arsenic (As)-doped silicon wafers are implanted at 10 keV and 80 keV with an implant dose of $3\times10^{15}$ atoms/cm$^3$. The samples are analyzed using a commercial Rigaku TXRF system with a rotating gold anode. Arsenic (As) atoms are excited by Au L$\beta$ radiation. For each angle, data from five points are acquired with a total measurement time was 500 s.

The As fluorescence yield (FY) is measured at several angles and reported in TABLE I. Fluorescence yield measurements are higher for the sample with low energy 10 keV implants than for the sample with high energy 80 keV implants presumably due to the higher As concentration in the near-surface region of the substrate. Most TXRF information relates to near-surface conditions of the substrate.

TABLE I

| Angle of Incidence $\alpha_1$(°) | 10 keV As FY (cps) | 80 keV As FY (cps) |
|---|---|---|
| 0.01 | 1.4 | 0.1 |
| 0.02 | 4.6 | 0.3 |
| 0.03 | 15 | 0.4 |
| 0.04 | 35 | 1.0 |
| 0.05 | 78 | 2.1 |
| 0.06 | 170 | 8.5 |
| 0.07 | 310 | 66 |
| 0.08 | 450 | 140 |
| 0.09 | 620 | 200 |
| 0.1 | 850 | 290 |
| 0.11 | 1180 | 350 |
| 0.13 | 2000 | 790 |

Figure 9:
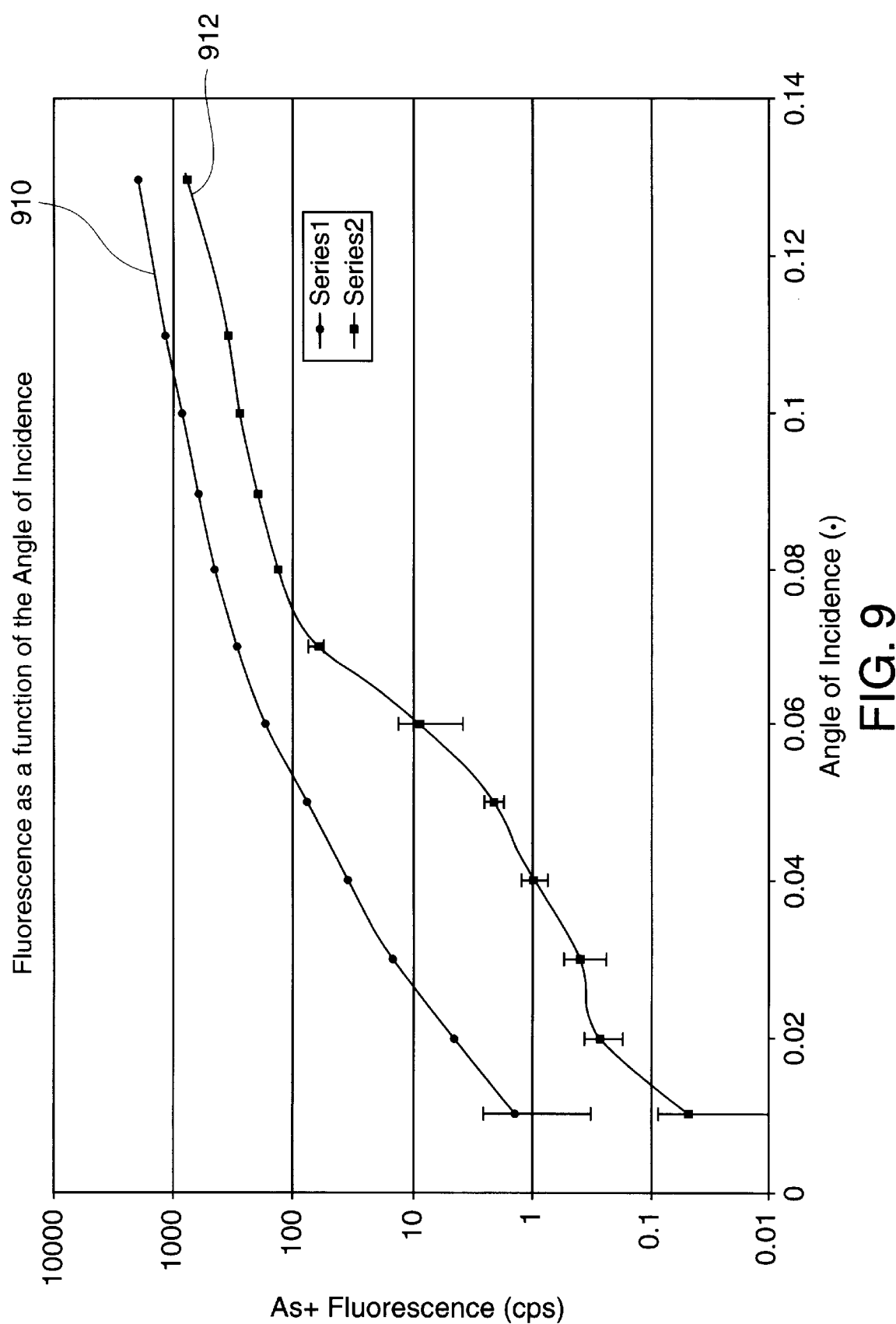
FIG. 9 is a graph that illustrates the relationship, determined by TXRF, of arsenic fluorescence yield (As FY) at varying angles of incidence $\phi_i$ for samples implanted at the same implant dose but different energies.

Referring to FIG. 9, a graph illustrates the relationship of arsenic fluorescence yield (As FY) at varying angles of incidence $\phi_i$ for samples implanted at the same implant dose but different energies of 10 keV and 80 keV.

The low-energy implant sample 910 has a higher arsenic fluorescence yield (As FY) than the high-energy implant sample 912 because the implant profile of the 10 keV implants 910 is closer to the surface than the 80 keV implants 912. Only the near surface region of the substrate generates counts (information) detected in the TXRF spectra.

For an energy of 12 keV and an angle of 0.01°, the depth penetration $z_n$ of the X-rays is approximately 4 nm. As the angles of incidence $\phi_i$ increases to 0.1°, the depth penetration $z_n$ increases to 6 nm.

Figure 11:
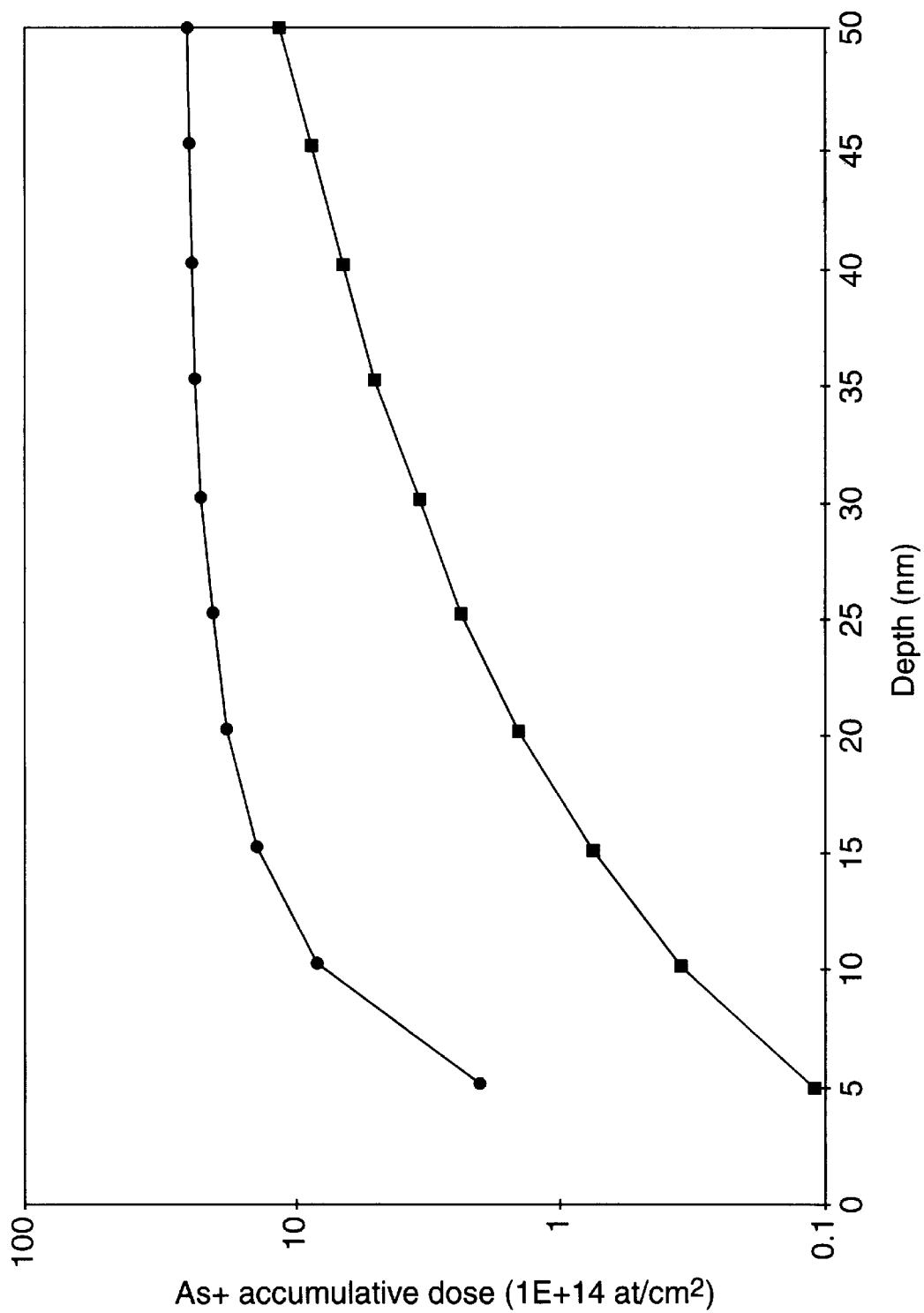
FIG. 11 is a graph that shows an integrated implant dose plotted against depth into the substrate that is determined using secondary ion mass spectroscopy (SIMS).

The fluorescence yield data obtained using TXRF is analyzed or calibrated using secondary ion mass spectroscopy (SIMS). Referring to FIG. 11, in an illustrative test a commercial Cameca IMS 6 F SIMS tool with a Cs ion source (10 keV) is used to determine an implant profile using a sample potential of 4.5 keV.

Figure 10:
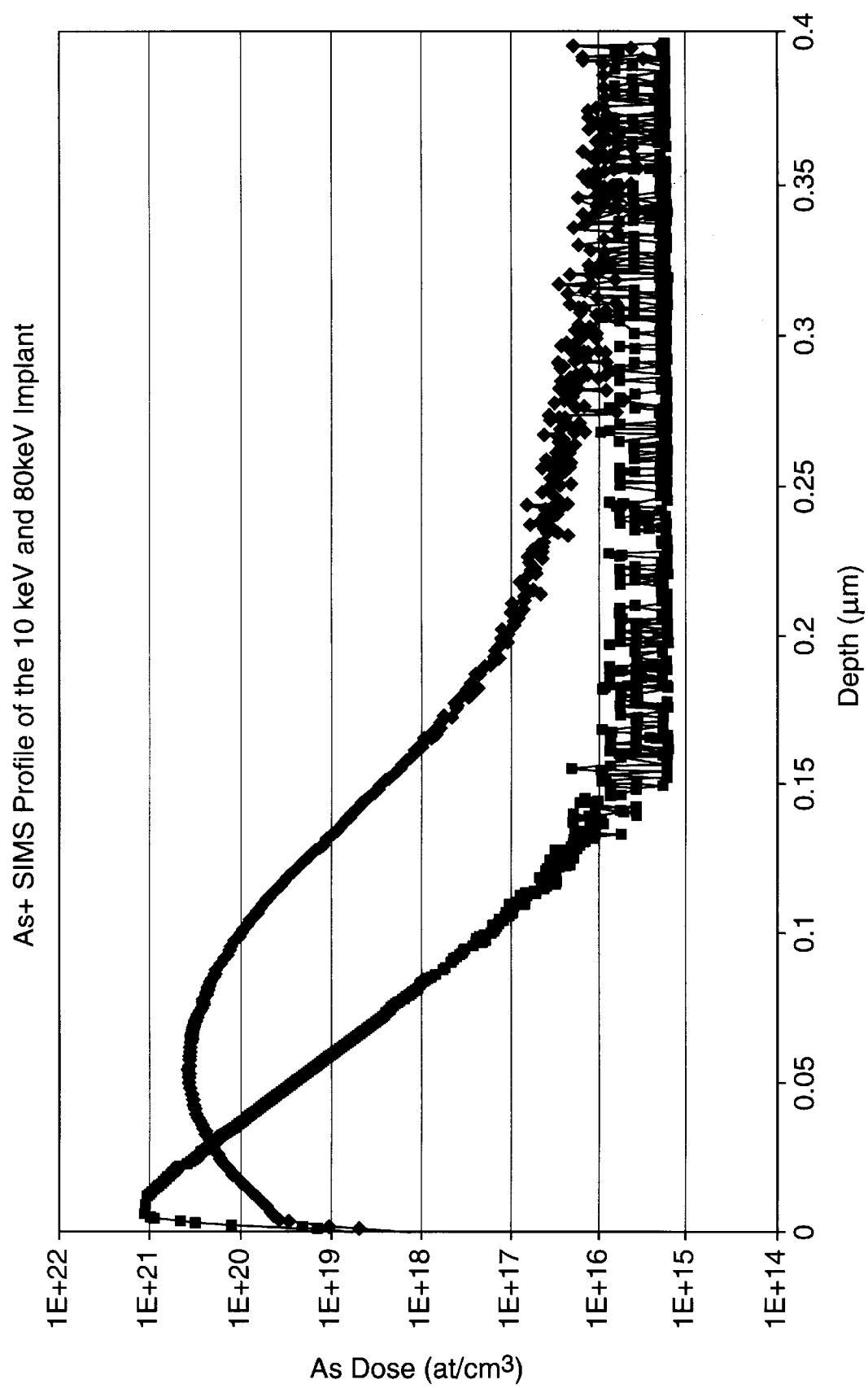
FIG. 10 is a graph of an arsenic (As) SIMS profile showing the arsenic dose of 10 keV and 80 keV samples at various depths in the substrate.

Referring to FIG. 10, a graph of an arsenic (As) SIMS profile showing the arsenic dose of 10 keV and 80 keV samples at various depths in the substrate. The accumulative dose is the integral of the SIMS profile. The increase of the As FY is much higher than the increase expected from SIMS data because the primary X-ray beam is divergent and also excites As at deeper layers. Thus, the measured FY is higher than the expected value.

The comparison between the SIMS accumulated As+ dose shown in FIG. 11 and the As FY at different angles shown in FIG. 9 are highly correlated, demonstrating a good correspondence between the SIMS and the TXRF data.

The TXRF technique is thus used to monitor ion implant doses and depth profiling of the implanted dopants. The application of TXRF is particularly suitable for ultra shallow implants of less than 200 Å which are used in 0.25 $\mu$m and smaller CMOS technologies. In comparison to other approaches which include chemical decomposition or sputter processes, the proposed procedure is nondestructive and can be applied in the semiconductor fabrication systems.

Figure 12:
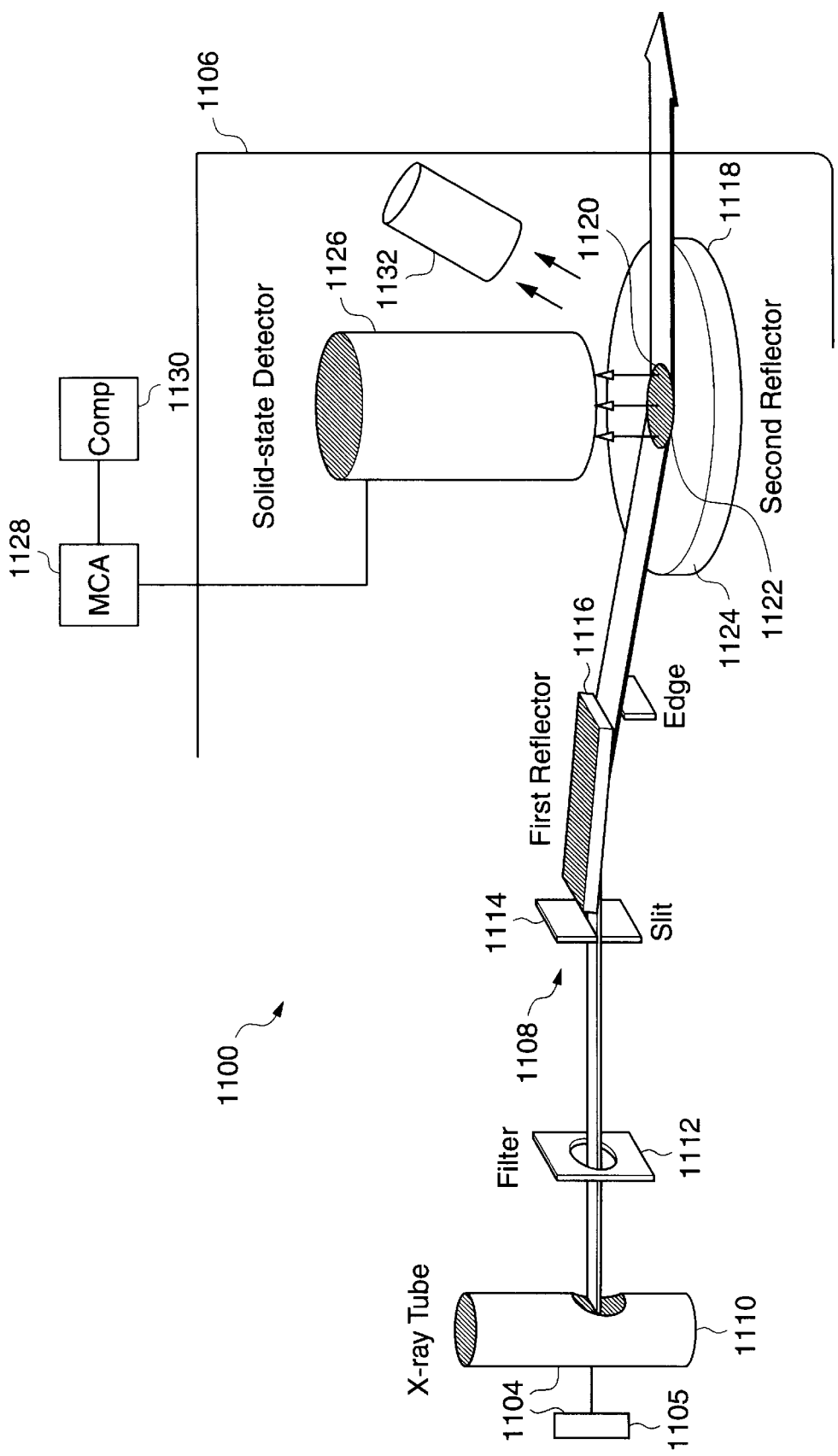
FIG. 12 is a schematic block diagram showing a total-reflection x-ray fluorescence (TXRF) spectrometer.

Referring to FIG. 12, a schematic block diagram shows a total-reflection x-ray fluorescence (TXRF) spectrometer 1100. TXRF spectrometry operates at grazing incident angles near the critical angles of total reflection of x-rays. At angles below the critical angle, the transmitted beam disappears and excitation of fluorescence radiation occurs only by an exponentially decaying energy transfer in the surface region of the test sample. The TXRF spectrometer 1100 includes a measuring chamber 1106 and a beam-forming pathway 1108. The beam-forming pathway 1108 includes an X-ray source 1104.

The X-ray source 1104 includes an X-ray generator 1105 and a high-power X-ray tube 1110 with a line focus that is, in various systems, a fixed anode tube or a rotating anode tube. The X-ray generator 1105 supplies the X-ray tube 1110 with high-potential power for an anode (not shown) and filament power for a cathode (not shown). The X-ray generator 1105 is a stable generator of conventional X-ray fluorescence and X-ray diffraction that delivers a rectified high voltage between 5 and 100 kV and a direct current of 5 to 500 mA, typically in increments of 1 kV and 1 mA, respectively. Output power typically reaches a maximum load of 3 to 30 kW.

The X-ray tube 1110 forms the primary X-ray beam for exciting a sample to fluorescence. Fine-focus X-ray tubes with a fixed anode are generally used for TXRF spectrometry. The X-ray tube 1110 forms a strip-like transmitted X-ray beam having a high intensity in a selected spectral region.

The X-ray beam is passed through a filter 1112 to increase selected signal peaks in relation to the spectral continuum. A suitable filter 1112 includes thin metal foils that are placed in front of the beam transmitted from the X-ray tube 1110. The thin metal foils or thin metal sheet operate as a selective attenuation filter that is inserted into the beam path to reduce a selected spectral peak or an entire energy band with respect to other spectral peaks or regions.

The X-ray beam is adapted to form a selected geometric shape and spectral distribution using diaphragms or collimator slits 1114 and a first reflector 1116. The beam is transmitted through the filter 1112 to a pair of precisely aligned diaphragms or collimator slits 1114 to change the geometric shape of the transmitted beam to a sheet or strip. Shaping of the beam is typically adapted through the usage of two collimator slits 1114 or by metallic edges that operate as diaphragms. For a system that uses metallic edges, silver, steel or platinum with a thickness of about 1 mm and a width of about 20 mm are fixed in self-contained devices are adjusted in modular components. The edges or slits 1114 form a strip-like beam having a thickness of about 10 $\mu$m.

Following the collimator slits 1114, the polychromatic beam from the X-ray tube 1110 is deflected by a first reflector 1116 that alters the primary spectrum of the beam. Various reflectors that may be suitable include low-pass filters, foil filters, and monochromators. For surface and thin-layer analysis, a monochromator is used as the first reflector 1116, although the monochromator is also useful for trace analysis. The monochromator is used as the first reflector 1116 for surface and thin-layer analysis since intensity profiles are to uniquely depend on glancing angle and not on photon energy. Monochromator types include natural crystals and multiple layers, either acting as Bragg reflectors, which differ in efficiency based on peak reflectivity and spectral bandwidth. For analysis of granular residues, one suitable type of reflector is a quartz glass block that acts as a totally reflecting mirror or low-pass beam filter that only cuts off the high-energy part of the bremscontinuum under grazing incidence.

After passing through the first reflector 1116, the primary beam strikes a sample carrier 1118 which includes a second reflector 1120 under grazing incidence. The sample carrier 1118 serves as a support for the sample and as a totally reflecting mirror. A total reflection at the sample carrier 1118 results when the primary X-ray beam strikes the sample carrier 1118 as a second reflector 1120 at a small angle of incidence. For X-ray photons of 60 keV, the glancing angle should be 0.015°. The divergence of the X-ray beam is even more constrained to a smaller angle. The glancing angle and divergence of the primary beam are increased to improve the intensity of the narrow primary beam and boost the effectiveness of excitation of lower energy photons that preferably induce excitation over high-energy photons. The increase in glancing angle and divergence of the primary beam are partly scattered, causing a significant background. To avoid the scattering and background, the first reflector 1116 acts as a low-pass or cutoff filter to eliminate high-energy photons.

The sample carrier 1118 is loaded with a sample substrate 1122 that is analyzed in the TXRF spectrometry process. A controllable positioner 1124 is attached to the sample carrier 1118 for positioning and tilting of the sample. The positioner 1124 controls the angle of incidence at which the transmitted beam strikes the sample. The angle of incidence is the controlled free variable that is varied to produce angular intensity profiles. The positioner 1124 holds the sample for presentation as a flat disk for total reflection of the primary beam. The positioner 1124 adjusts the position of the sample in a reference plane and tilts the sample around a horizontal axis. The angle of incidence is variable in a stepwise manner. The positioner 1124 permits displacement of the sample to set any spot of a large sample area in a measuring position and check the total surface of the sample. The positioner 1124 typically includes a plurality of stepper motors for controlling multiple different movements.

The fluorescence radiation of the sample is detected and registered as an X-ray spectrum using an energy-dispersive spectrometer. Reflections of the beam from the sample form a fluorescence intensity that is recorded using an energy-dispersive solid-state detector 1126. A typical solid-state detector 1126 is a Si(Li) detector. X-ray photons emitted from the sample are directly collected by a semiconductor detector that counts individual photons and determines the energies of the photons. The semiconductor detector produces an individual voltage pulse for each collected photon, the voltage pulse having an amplitude that is proportional to the energy of the photon. The solid-state detector 1126 is mounted perpendicular to the plane surface of the sample carrier 1118 to measure spectra with a minimum scattered background. The solid-state detector 1126 is positioned about 1 millimeter from the sample to detect fluorescence radiation within a large solid angle. A typical solid-state detector 1126 is a pure silicon or germanium crystal that is several millimeters wide and thick, and is highly resistive. The frontal areas of the crystal are coated with electrodes formed from thin layers of gold. An inverse DC voltage is applied to the electrode to define the direction of low conductivity of a small leakage current despite a large voltage of −500V to −1000V. The configuration is termed a p-i-n diode with a reverse bias.

The solid-state detector 1126 detects X-ray photons as follows. An incident X-ray photon interacts with the crystal and ionizes the crystal atoms, creating photoelectrons and Auger electrons. The electrons pass energy in several steps and raise outer electrons from the valence band into the conduction band of the crystal lattice. Electron holes are simultaneously created in the valence band. A complete tracking of the electron-hole pairs is produced until all energy in the incident photon is consumed. Due to the high applied voltage, the electron-hole pairs separate and the electrons and electron holes drift to the positive electrode and the negative electrode, respectively. A charge pulse is produced that is useful for counting of single photons. The number of electron-hole pairs is directly proportional to the energy of the photon that is detected, the magnitude of the charge pulse corresponds to the energy of the detected photon. Thus, the semiconductor solid-state detector 1126 counts single X-ray photons and reads the energies of the photons.

The individual detector pulses are processed in an electronic measuring chain and sorted by a multiple-channel analyzer 1128. Thus, the multiple-channel analyzer 1128 measures the fluorescence intensity reflected from the sample and generates an energy-dispersive spectrum. The multiple-channel analyzer 1128 amplifies, shapes, and sorts the charge pulses produced by the solid-state detector 1126 and counts pulses in multiple selected amplitude categories. Pulse amplitude is an accurate measure of the energy of detected photons. The spectrum is available for further processing by a dedicated computer 1130.

In some systems, reflectivity measurement are performed by an additional detector 1132. The primary beam that is monochromatized by the first reflector 1116 is reflected at a layered or unlayered substrate. The intensity of the reflected beam is measured by a second simple detector 1132 such as a photodiode or scintillation detector. The second simple detector 1132 is tilted at a double angle $2\alpha$ when the layered sample is tilted at a single angle $\alpha$, both angles being tilted around an axis a in the horizontal plane of the sample carrier 1118.

Measurements are generally performed in ambient air. However, in some measurements, the measuring chamber 1106 is flushed with nitrogen to suppress the argon-peak from ambient air. In some measurements for detecting low-energy peaks of low-Z elements, a helium flush or a vacuum chamber are used.

Other suitable TXRF spectrometry systems may be formed by assembling the described filters and diaphragms in other arrangements that are known in the art.

Figure 13:
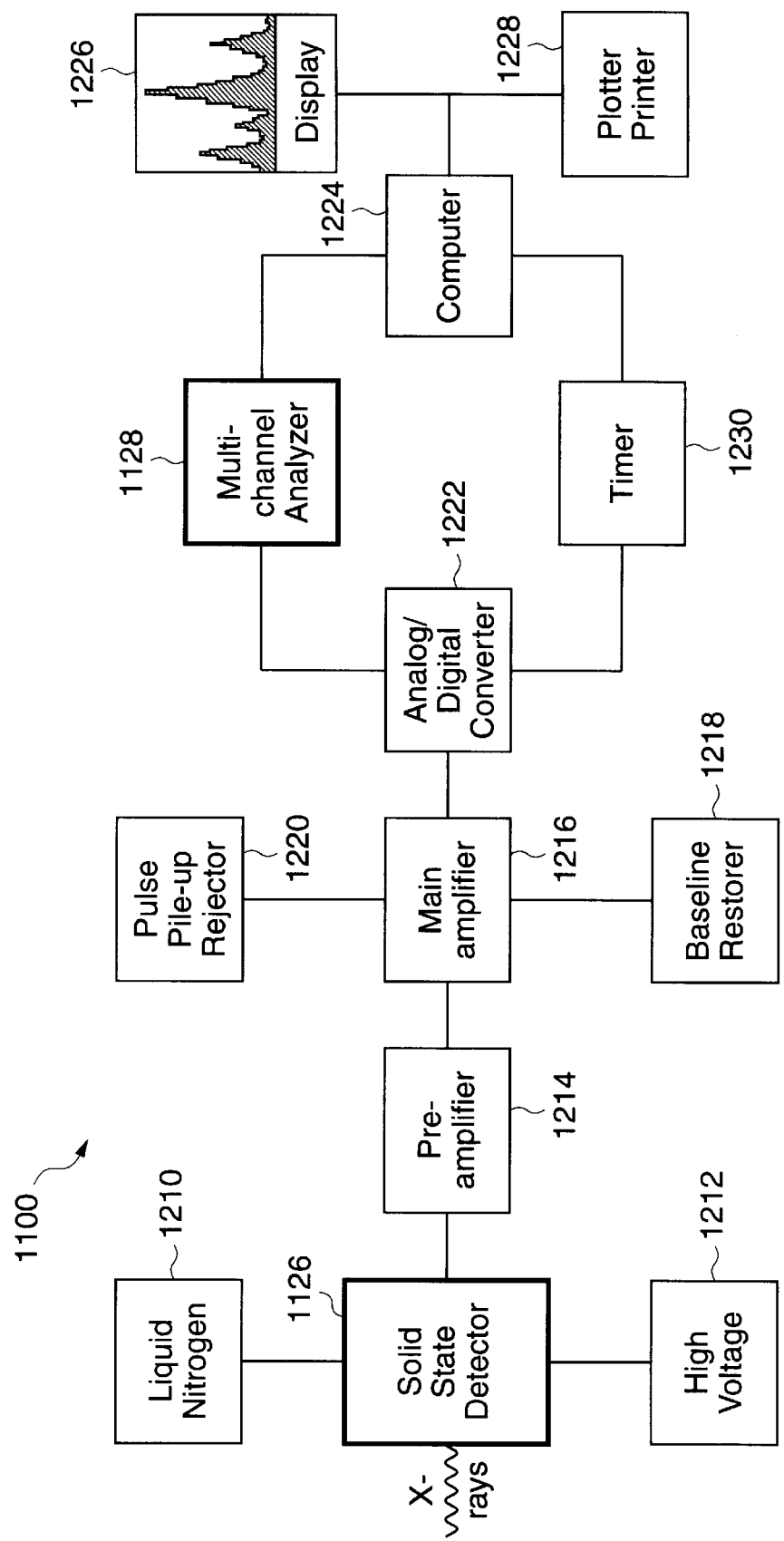
FIG. 13 is a schematic block diagram that illustrates devices and interconnections of a solid-state detector and multi-channel analyzer of the total-reflection x-ray fluorescence (TXRF) spectrometer.

Referring to FIG. 13, a schematic block diagram illustrates devices and interconnections of the solid-state detector 1126 and the multiple-channel analyzer 1128 in one example of the TXRF spectrometer 1100. The solid-state detector 1126 is connected to a copper rod that is immersed in liquid nitrogen 1210 and powered by a high voltage source 1212.

A signal path from the solid-state detector 1126 is connected to a FET-based preamplifier 1214 and a main amplifier 1216 with a baseline restorer 1218 and a pulse pile-up rejector 1220. The preamplifier 1214 converts charge pulses generated by the solid-state detector 1126 to low-voltage pulses. The amplitudes or pulse heights are proportional to the number of electron-hole pairs and thus to the energies of the detected X-ray photons. The preamplifier 1214 is installed in close proximity to the solid-state detector 1126 and cooled to the temperature of liquid nitrogen 1210 to reduce electronic noise. The main amplifier 1216 is a high-gain linear amplifier that amplifies millivolt pulses to voltage levels.

The pulse pile-up rejector 1220 reduces distortion that results from pulse shaping. The pulses are shaped to a selected form with different amplitudes but with a constant shaping time. The shaping time is sufficiently high, for example 6 or 8 $\mu$s, to suppress noise, but at the expense of increasing the probability of pulse overlap. When coinciding pulses overlap, a "pulse pile-up effect" occurs in which a single pulse is incorrectly registered having an amplitude that is the sum of individual pulse amplitudes. The pulse pile-up rejector 1220 avoids pile-up for instances in which the two pulses are not coincident in time but rather arrive 1 $\mu$s apart. The nearly coincident pulses are "rejected" and lost in the counting. The loss of counts is compensated by a suitable extension of measuring time.

The baseline restorer 1218 reduces distortion that results when the pile-up effect becomes serious at high count rates in which pulses are not only coincident but also partially overlapping. The partial overlapping causes the baseline of the main amplifier 1216 to shift to a higher voltage so that the output pulses appear reduced or depressed below the true amplitude.

Output pulses from the main amplifier 1216 are applied to an analog-to-digital converter (ADC) 1222 to generate a digital number that corresponds to the analog amplitude of the pulses. The digital number is sent as an address to the multiple-channel analyzer 1128. The multiple-channel analyzer 1128 sorts the pulses by address and counts the number of pulses at a particular address. Data stored in the memory of the multiple-channel analyzer 1128 in the manner of a content-addressable memory (CAM) in which each address corresponds to a pulse of a particular amplitude and the data at the address corresponds to the number of counts at the particular amplitude. The memory locations correspond to channels separated into small energy ranges. In one example, the multiple-channel analyzer 1128 contains 1000 channels that are assigned to consecutive increments of 10, 20 or 40 eV that are indicative of the energy of X-ray photons.

Digital data from the multiple-channel analyzer 1128 is applied to a computer 1224 which typically converts the raw digital data to an energy-dispersive spectrum that is displayed on monitor 1226 or plotted on a plotter/printer 1228. The spectrum is typically arranged for display as a histogram showing the counts in relation to energy. The computer 1224 controls the monitor 1226, the plotter/printer 1228, and a timer 1230. The timer 1230 begins and terminates measurements or data collection at a selected time.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims. For example, the described TXRF system is described for illustrative purposes only and the described techniques for analysis of samples may be performed on any suitable TXRF device or other X-ray fluorescence device that suitable signals for measuring implant dose in a substrate.

What is claimed is:

1. A method of measuring a depth profile of an element in a substrate comprising:

acquiring a plurality of first X-ray fluorescence measurements from a substrate having a known implant profile distribution for a selected element;

acquiring a plurality of second X-ray fluorescence measurements from a substrate having an unknown implant profile distribution for the selected element;

determining a plurality of X-ray fluorescence ratios comparing the first X-ray fluorescence measurements and the second X-ray fluorescence measurements;

acquiring a plurality of first control measurements from a substrate having a known implant profile distribution for the selected element;

acquiring a plurality of second control measurements from a substrate having an unknown implant profile distribution for the selected element;

determining a plurality of control ratios comparing the first control measurements and the second control measurements; and deriving a calibration coefficient from a comparison of the plurality of X-ray fluorescence ratios and the plurality of control ratios.

2. A method according to claim 1 further comprising:

acquiring the plurality of first and second control measurements from a substrate using secondary ion mass spectroscopy (SIMS).

3. A method according to claim 1 further comprising:

acquiring the plurality of first and second control measurements from a substrate using simulated profiles.

4. A method according to claim 1 further comprising:

acquiring the X-ray fluorescence measurements using a total reflection X-ray fluorescence (TXRF) type system; and acquiring the plurality of first and second control measurements from a substrate using secondary ion mass spectroscopy (SIMS).

5. A method according to claim 4 wherein:

the TXRF-type system generates data in the form of count ratios; and

SIMS generates data in the form of integrals of SIMS profiles so that the calibration coefficient is determined by comparing count ratios to integrals of SIMS profiles.

6. A method according to claim 1 further comprising:

acquiring the X-ray fluorescence measurements using a total reflection X-ray fluorescence (TXRF) type system; and acquiring the plurality of first and second control measurements from a substrate using simulated profiles.

7. A method according to claim 6 wherein:

the TXRF-type system generates data in the form of count ratios; and

SIMS generates data in the form of integrals of simulated profiles so that the calibration coefficient is determined by comparing count ratios to integrals of simulated profiles.

8. A method according to claim 1 further comprising:

acquiring a X-ray fluorescence data from a substrate having an unknown implant profile distribution for the selected element; and forming a depth profile distribution of the element as a function of the acquired X-ray fluorescence data and the calibration coefficient.

9. A method according to claim 8 further comprising:

varying an angle of incidence of the X-ray fluorescence measurements, differing angles of incidence relating to differing probe depths into the substrate.

10. A method according to claim 8 further comprising:

varying an angle of incidence of the X-ray fluorescence measurements in a range between 0.8 and 1.0 times a critical angle of total reflection $\phi_{crit}$.

11. A method according to claim 10 further comprising:

using a small angle divergence of the primary X-ray beam to vary the angle of incidence in the range between 0.8 and 1.0 times a critical angle of total reflection $\phi_{crit}$.

12. A method according to claim 8 wherein:

the X-ray fluorescence measurements and X-ray fluorescence data are acquired using a total reflection X-ray fluorescence (TXRF) type system.

13. A method according to claim 12 wherein:

acquiring X-ray fluorescence measurements and the X-ray fluorescence data further includes:

illuminating the substrate with a primary incident X-ray beam at an incident angle;

varying the incident angle of the X-ray beam through a plurality of small angles near a critical angle; and acquiring a series of X-ray fluorescence measurements at the respective plurality of small angles.

* * * * *